(12) United States Patent
Schaer

(10) Patent No.: US 7,331,960 B2
(45) Date of Patent: Feb. 19, 2008

(54) LINEAR ABLATION ASSEMBLY

(75) Inventor: Alan K Schaer, San Jose, CA (US)

(73) Assignee: CaRDiMa, Inc.

( * ) Notice: Subject to any disclaimer, the term of this patent is extended or adjusted under 35 U.S.C. 154(b) by 638 days.

(21) Appl. No.: 10/980,699

(22) Filed: Nov. 3, 2004

(65) Prior Publication Data

US 2005/0065512 A1    Mar. 24, 2005

Related U.S. Application Data

(60) Division of application No. 09/901,856, filed on Jul. 9, 2001, now Pat. No. 6,814,732, which is a division of application No. 09/182,967, filed on Oct. 29, 1998, now Pat. No. 6,302,880, which is a continuation-in-part of application No. 08/629,057, filed on Apr. 8, 1996, now Pat. No. 5,863,291.

(51) Int. Cl.
  *A61B 18/18*    (2006.01)
(52) U.S. Cl. .................. 606/41; 607/101; 607/122; 600/374
(58) Field of Classification Search .............. 606/41, 606/42, 45–50; 607/101, 115, 116, 119, 607/122; 600/372–374
See application file for complete search history.

(56) References Cited

U.S. PATENT DOCUMENTS

| 3,910,279 | A |   | 10/1975 | Okada et al. |
| 5,163,938 | A |   | 11/1992 | Kambara et al. |
| 5,242,441 | A | * | 9/1993  | Avitall ................... 606/41 |
| 5,242,443 | A |   | 9/1993  | Kambin |
| 5,263,493 | A |   | 11/1993 | Avitall |
| 5,313,943 | A |   | 5/1994  | Houser et al. |

(Continued)

FOREIGN PATENT DOCUMENTS

EP    554 722    8/1993

(Continued)

OTHER PUBLICATIONS

Supplementary European Search Report in EP Application No. EP 99 907 1286, mailed Apr. 6, 2005.

*Primary Examiner*—A. Farah
(74) *Attorney, Agent, or Firm*—Edward J. Lynch

(57) ABSTRACT

An intravascular device for the formation of linear lesions which has particular utility in the treatment of atrial fibrillation and flutter. The intravascular device has an outer delivery member with a distal section which has an elongated opening and a support element coextending with the opening. An EP device having a plurality of electrodes on its distal section is slidably disposed within the inner lumen of the delivery member but it is secured by its distal end within the distal extremity of the delivery member at least while in operation. In this manner an axial force in the proximal direction on the proximal extremity of the EP device, which extends out of the patient during the procedure, will cause the distal shaft section of the EP device to arch outwardly out of and away from the distal section of the delivery shaft along an inner side of the curved distal section and engage the surface of the patient's heart chamber. RF electrical energy delivered to the electrodes on the distal shaft section of the EP device will form a linear lesion which terminates the fibrillation or flutter.

46 Claims, 16 Drawing Sheets

U.S. PATENT DOCUMENTS

| | | | |
|---|---|---|---|
| 5,323,768 A | 6/1994 | Saito et al. | |
| 5,341,807 A | 8/1994 | Nardella | |
| 5,363,861 A | 11/1994 | Edwards et al. | |
| 5,431,696 A | 7/1995 | Atlee, III | |
| 5,454,370 A | 10/1995 | Avitall | |
| 5,482,037 A | 1/1996 | Borghi | |
| 5,487,385 A * | 1/1996 | Avitall | 600/374 |
| 5,555,883 A | 9/1996 | Avitall | |
| 5,687,723 A | 11/1997 | Avitall | |
| 5,863,291 A * | 1/1999 | Schaer | 606/41 |
| 6,001,093 A | 12/1999 | Swanson et al. | |
| 6,302,880 B1 * | 10/2001 | Schaer | 606/41 |
| 6,454,758 B1 * | 9/2002 | Thompson et al. | 604/528 |
| 6,814,732 B2 * | 11/2004 | Schaer | 606/41 |
| 7,004,938 B2 * | 2/2006 | Ormsby et al. | 606/33 |
| 7,029,471 B2 * | 4/2006 | Thompson et al. | 606/41 |
| 7,070,595 B2 * | 7/2006 | Ormsby et al. | 606/33 |
| 7,104,990 B2 * | 9/2006 | Jenkins et al. | 606/49 |
| 7,182,764 B2 * | 2/2007 | Jenkins et al. | 606/41 |

FOREIGN PATENT DOCUMENTS

| | | |
|---|---|---|
| EP | 609 182 | 8/1994 |
| WO | WO 92/19167 | 11/1992 |
| WO | WO 94/16619 | 8/1994 |
| WO | WO 95/10322 | 4/1995 |
| WO | WO 95/15115 | 6/1995 |
| WO | WO 95/34259 | 12/1995 |
| WO | WO 97/37607 | 10/1997 |

* cited by examiner

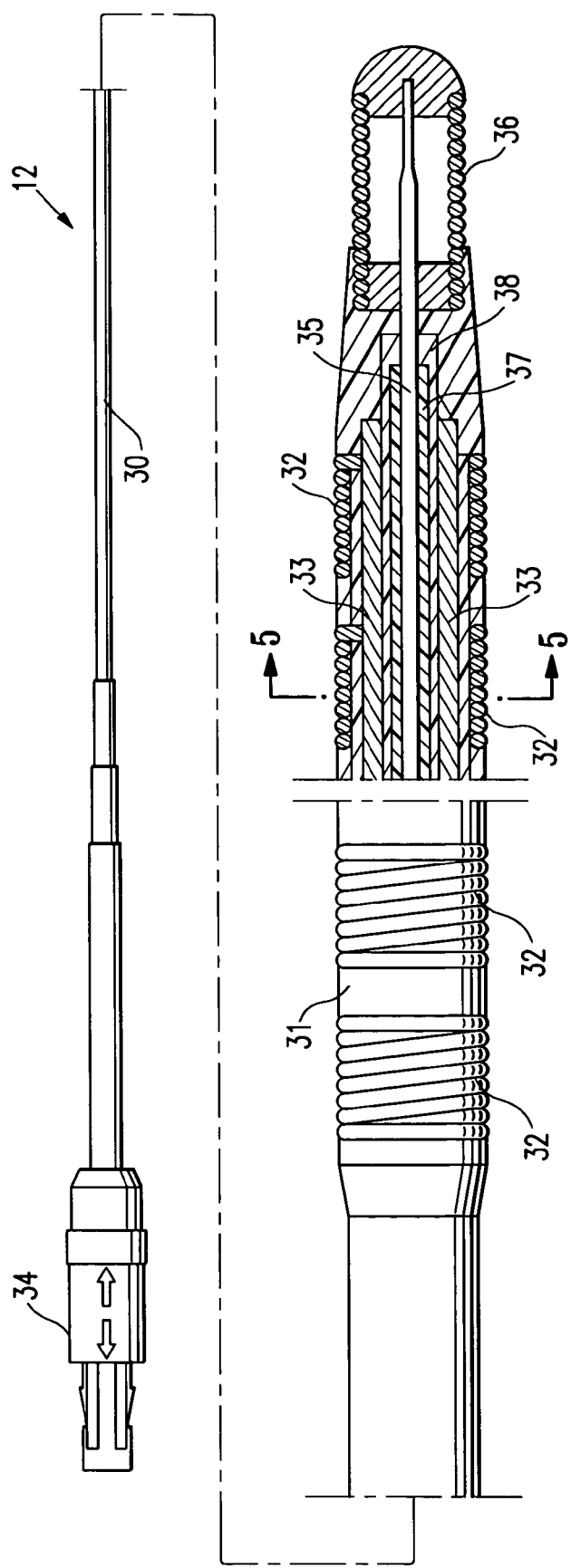
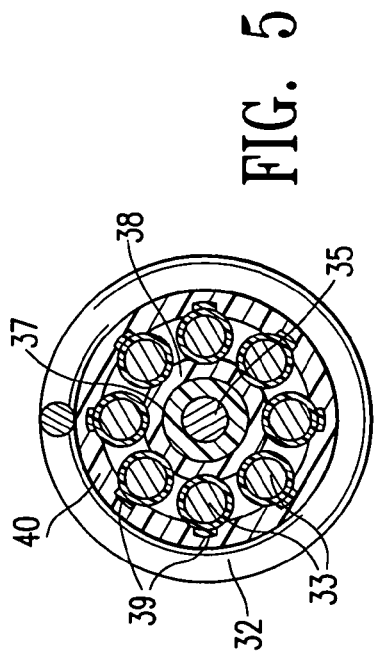
FIG. 4
FIG. 5

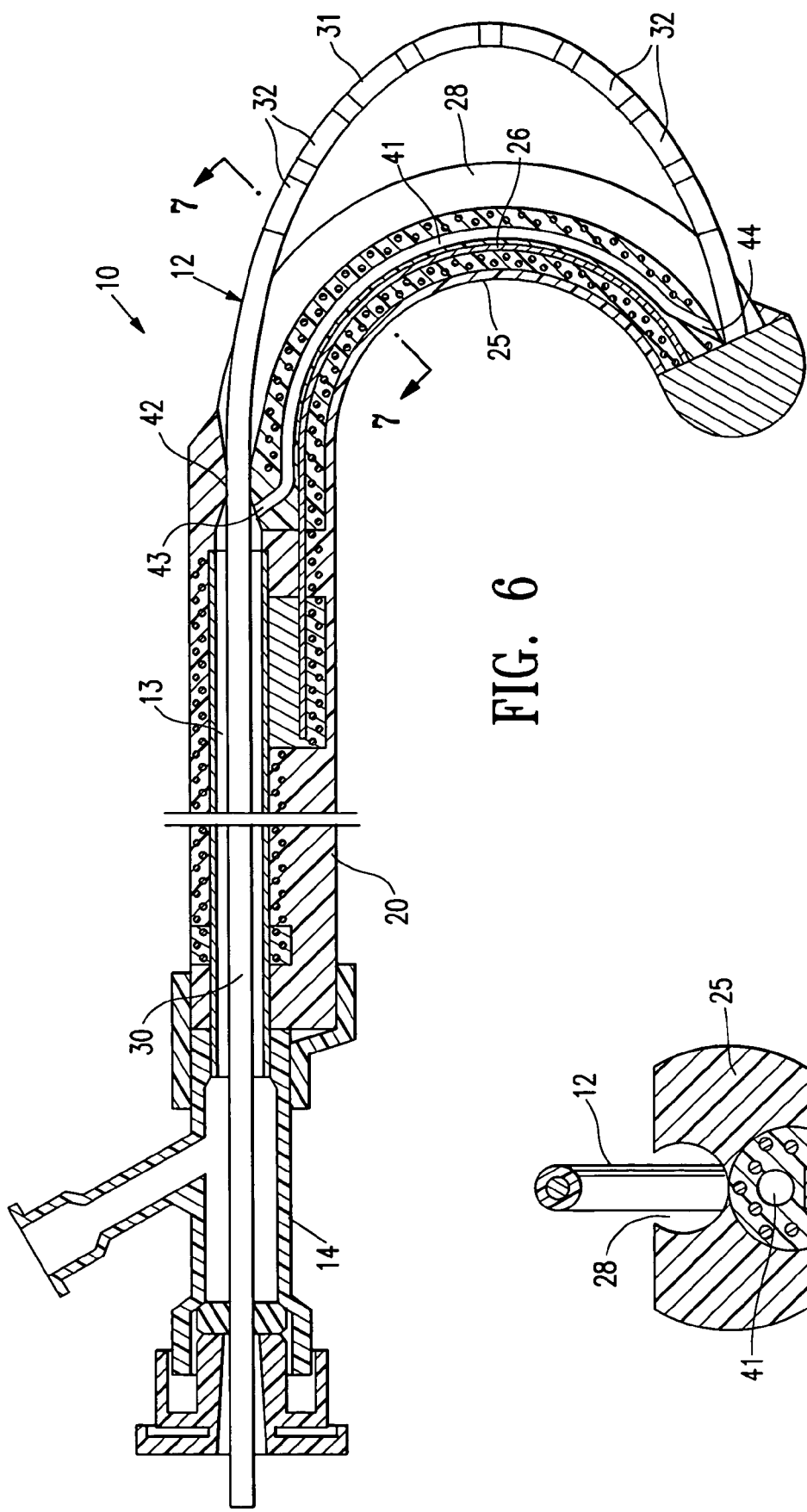

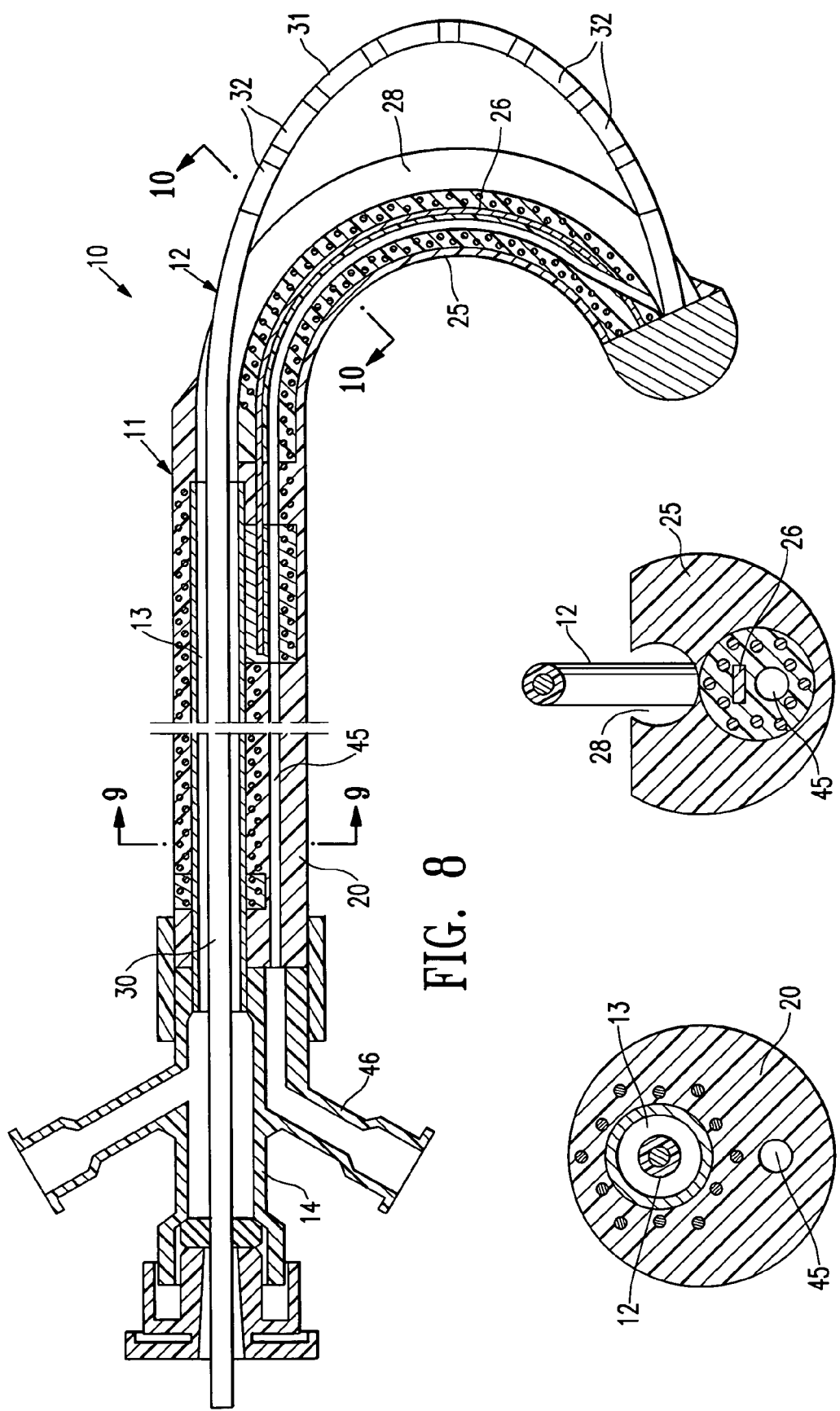

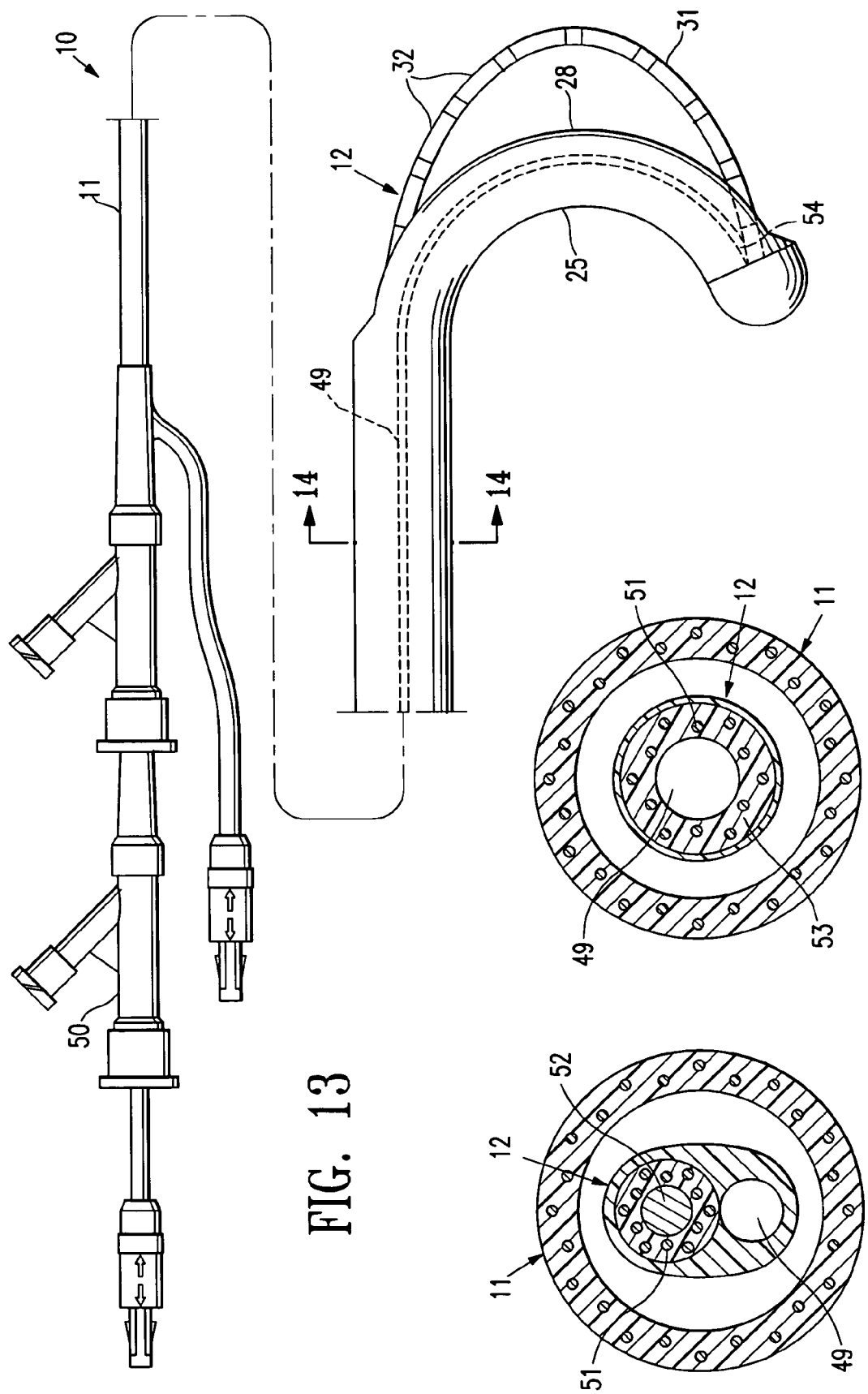

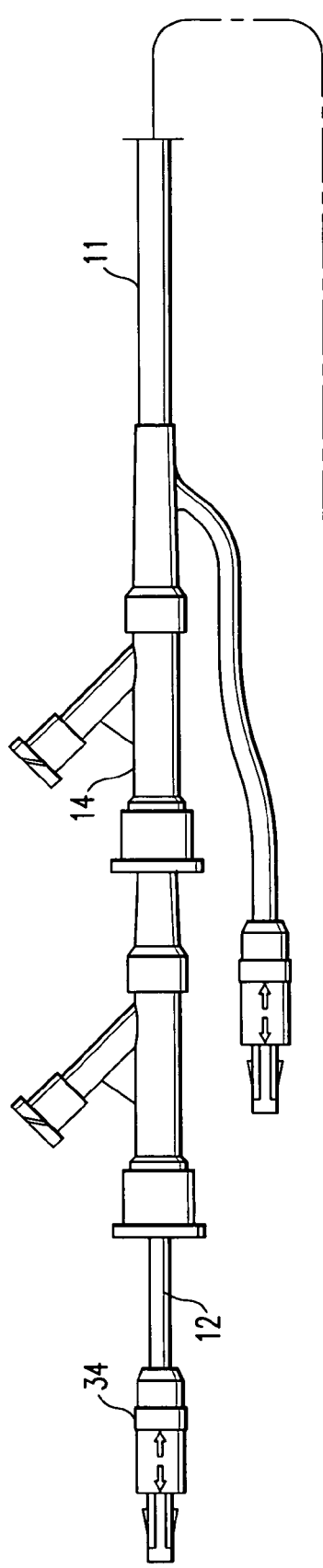
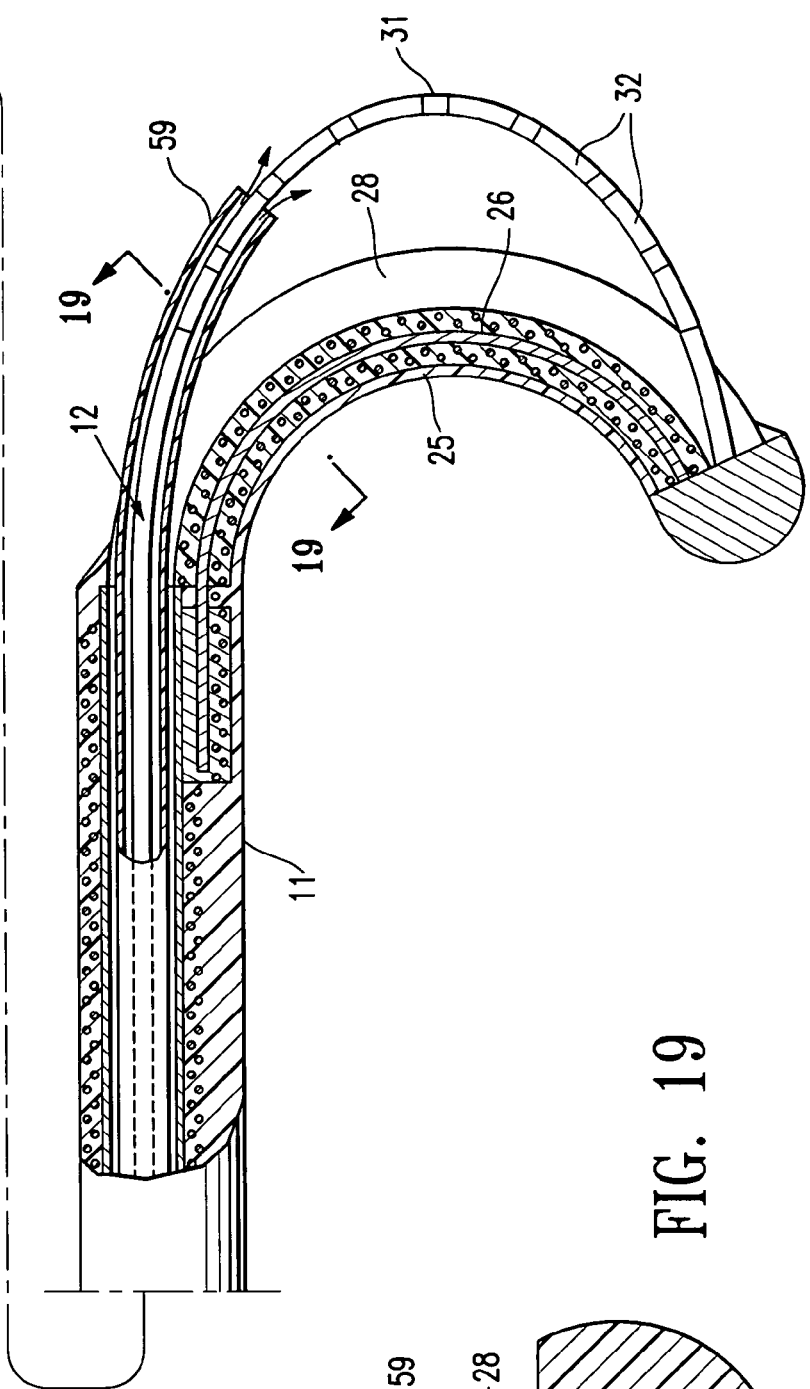
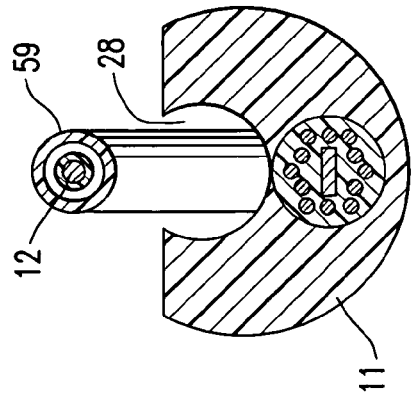
FIG. 18
FIG. 19

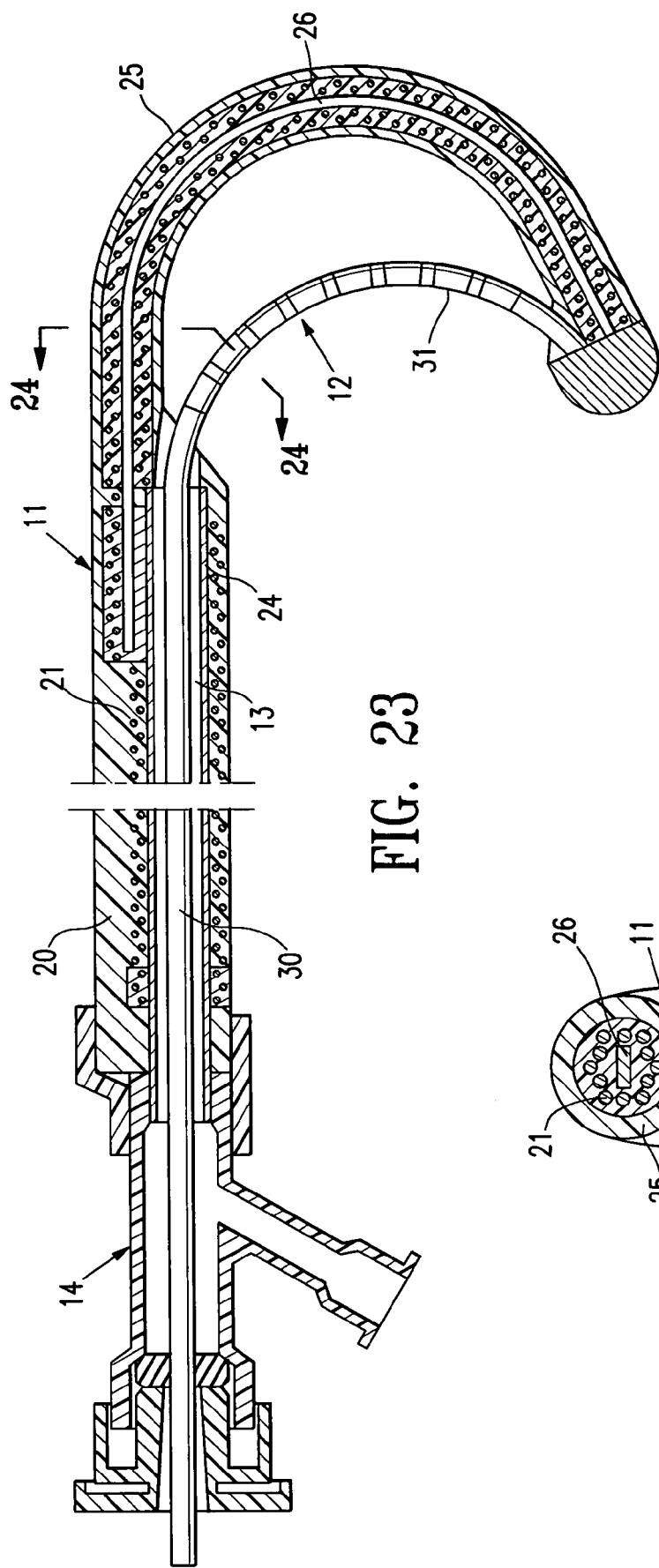
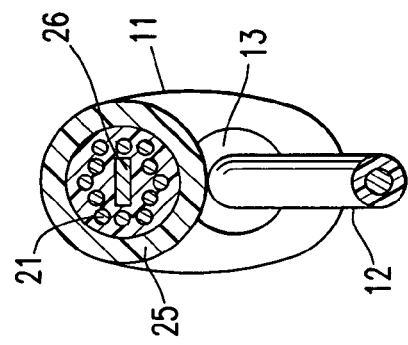
FIG. 23
FIG. 24

LINEAR ABLATION ASSEMBLY

RELATED APPLICATIONS

This application is a divisional of application Ser. No. 09/901,856, filed Jul. 9, 2001, now U.S. Pat. No. 6,814,732, which is a divisional of Ser. No. 09/182,967, filed Oct. 29, 1998, now U.S. Pat. No. 6,302,880, which is a continuation-in-part of Ser. No. 08/629,057, filed Apr. 8, 1996, now U.S. Pat. No. 5,863,291, which are incorporated herein in its entireties by reference and which priorities are claimed.

BACKGROUND OF THE INVENTION

This invention is a continuation-in-part of U.S. patent application Ser. No. 08/629,057, entitled LINEAR ABLATION ASSEMBLY, filed Apr. 8, 1996, the disclosure of which is incorporated by reference herein.

This invention generally relates to the detection and elimination of cardiac arrhythmia and particularly atrial fibrillation.

Atrial fibrillation is the disorganized depolarization of a patient's atrium with little or no effective atrial contraction. This condition may be chronic or intermittent, and it presently affects approximately 2 million or more people in the United States alone. For atrial fibrillation refractory to conventional drug therapy, it has been conventional practice to make incisions in the atrial wall, to surgically segregate the tissue thereof, to discontinue the atrial fibrillation. The atrial segments formed by the surgical segregation are electrically isolated and too small to allow the fibrillation to continue. However, the surgical technique is quite traumatic and is unacceptable to a large fraction of those patient's experiencing atrial fibrillation or flutter. Avitall in U.S. Pat. No. 5,487,385 discloses the use of high frequency electrical energy with a specific intravascular electrophysiological (EP) device to form linear ablations within a patient's atrial chamber to provide results similar to the surgical techniques in terminating atrial fibrillation but with significantly reduced trauma. However, the Avitall device cannot be readily placed within the patient's atrial chamber and provide the necessary contact between the electrodes on the device and the atrial tissue to generate linear lesions of a requisite length when RF electrical energy is emitted from the electrodes.

What has been needed is an ablation assembly which can be readily manipulated within a patient's atrial chamber to generate effective linear lesions at any desired location within the atrial chamber. The present invention satisfies these and other needs.

SUMMARY OF THE INVENTION

This invention is directed to an intravascular assembly suitable for forming linear ablations within a chamber of a patient's heart, which is particularly suitable for treating atrial fibrillation and flutter.

In a broad sense the assembly of the invention comprises a delivery member with an inner lumen extending therein, and an elongated support element in a distal section of the delivery member, and an elongated EP device disposed within the inner lumen of the delivery member and fixed by its distal end within the distal portion of the delivery member. The elongated support element is coextensive at least in part with an elongated opening in a distal section of the delivery member.

Longitudinal movement of the EP device within the inner lumen of the delivery member causes the distal portion of the EP device to arcuately extend out and away from the distal section of the delivery member. The supporting member in the distal portion of the delivery member provides support to the distal end of the EP device and ensures that the distal portion of the EP device completely engages the inner surface of the patient's heart chamber along a length thereof for emitting high frequency (RF) electrical energy for the purpose of effective linear ablation of heart tissue within the patient's heart chamber. Additionally, the electrode may be used for the collection of electrical signals from the surface of the atrial chamber.

Effective detection of electrical activity is necessary to accurately locate the arrythmogenic site where the linear ablation is to occur and for effective tissue ablation in a linear fashion to isolate sections of the atrial wall defining the heart chamber. The EP device of the assembly has a plurality of electrodes on the distal portion thereof which may be used for both sensing or ablating. The outer dimensions of the distal portion of the EP device are generally less than 5 Fr., preferably less than 4 Fr., in diameter.

In one presently preferred embodiment, the supporting member of the delivery member is a metallic ribbon which has an elongated flat surface which faces the elongated opening in the distal section of the delivery member. It may be made from high strength materials such as stainless steel, pseudoelastic NiTi alloys in an austenite phase. The support element is preferably manually shaped into a curved or angled condition to facilitate entry of the distal extremity of the assembly within the patient's heart chamber, particularly the right atrium, and the proper positioning of the extended distal section of the EP device against the inner surface of the heart chamber. Additionally, an elongated deflection line may be provided in a wall of the delivery member, for deflecting the distal section of the delivery member into a curved or angled condition.

The inner radius of the extended distal section of the EP device is controlled by the length of the elongated opening in the delivery member and the distance the EP device is spaced from the support element. The effective length of the elongated opening can be controlled by the longitudinal location of the distal end of a sheath disposed about the exterior of the delivery member. As the distal end of the sheath extends distally, the effective length of the elongated opening in the distal section of the delivery member is shortened and the radius of curvature of the distal section of the EP device is correspondingly decreased.

BRIEF DESCRIPTION OF THE DRAWINGS

FIG. 4 is an elevational view, partially in section, of an EP device suitable for use with the assembly shown in FIGS. 1-5.

FIG. 5 is a transverse cross-sectional view of the EP device shown in FIG. 4 taken along the lines 5-5.

FIG. 6 is a longitudinal cross-sectional view of an alternative embodiment similar to that shown in FIG. 1 wherein a lumen is provided to deliver fluid to the distal extremity of the assembly.

FIG. 7 is a transverse cross-sectional view of he assembly shown in FIG. 6 taken along the lines 6-6.

FIG. 8 is a longitudinal cross-sectional view of an alternative embodiment similar to that shown in FIG. 6 with a lumen extending from the proximal end of the assembly to the distal end of the assembly.

FIG. 9 is a transverse cross-sectional view of he assembly shown in FIG. 8 taken along the lines 9-9.

FIG. 10 is a transverse cross-sectional view of he assembly shown in FIG. 8 taken along the lines 10-10.

FIG. 13 is an elevational view of another embodiment wherein the EP device of the assembly is provided with an inner lumen for delivery of fluid.

FIG. 14A is a transverse cross-sectional view of the embodiment shown in FIG. 13 taken along the lines 14-14.

FIG. 14B is a transverse cross-sectional view of an alternative embodiment of that shown in FIG. 13 taken along the lines 14-14.

FIG. 18 is an elevational view, partially in section, of an alternative embodiment wherein a longitudinally movable flush sheath is provided about the EP device of the assembly to delivery fluid to desired locations on the distal section thereof.

FIG. 19 is a transverse cross-sectional view of the embodiment shown in FIG. 18 taken along the lines 19-19.

FIG. 23 is an elevational view, partially in section, of an alternative embodiment of the assembly shown in FIG. 20 having an elongated depression.

FIG. 24 is a transverse cross-sectional view of the assembly shown in FIG. 24 taken along the lines 24-24

DETAILED DESCRIPTION OF THE INVENTION

Figures 1, 2, 3:
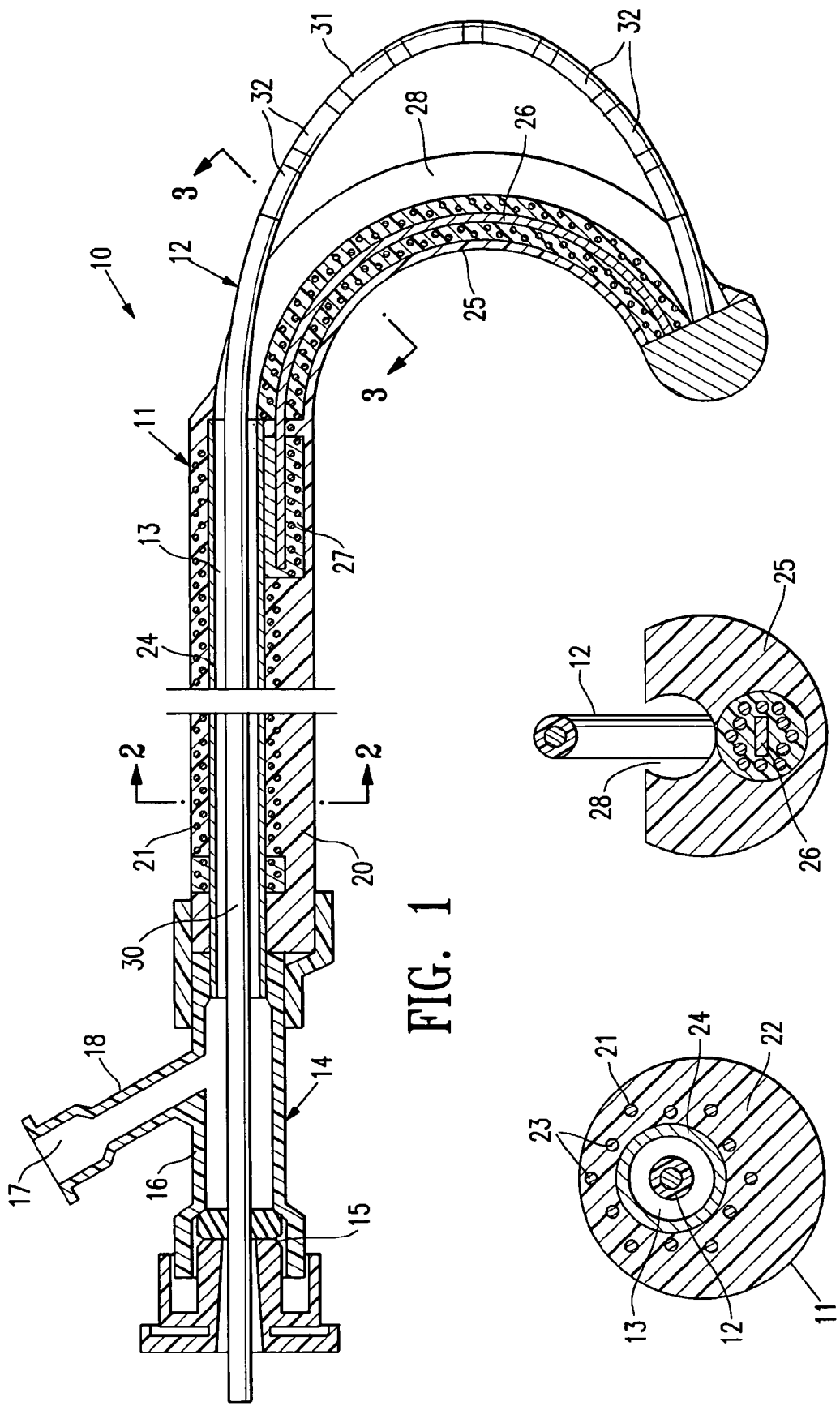
FIG. 1 is an elevational view, partially in section, of a mapping and ablation assembly embodying features of the invention.
FIG. 2 is a transverse cross-sectional view of the assembly shown in FIG. 1 taken along the lines 2-2.
FIG. 3 is a transverse cross-sectional view of the assembly shown in FIG. 1 taken along the lines 3-3.

FIGS. 1-3 schematically depict a mapping/ablation assembly 10 embodying features of the invention which generally comprises a delivery member 11 and an elongated EP device 12 slidably disposed within the inner lumen 13 of the delivery member 11 with the distal end of the EP device secured within the delivery member 11. An adapter 14 is provided on the proximal end of the delivery member 11 with a hemostatic valve 15 on the proximal end of the central arm 16 of the adapter and with a flush port 17 in the proximal end of the side arm 18.

The delivery member 11 has a proximal shaft section 20 which is formed of a braided tubular structure 21 with a polymer impregnate 22 incorporated therein. The braided structure 21 may be formed of high strength filaments 23 (e.g. 6×6 strands) such as stainless steel wire with a typical diameter of about 0.003 inch (0.08 mm). The polymer impregnate is preferably a thermoplastic polyurethane such as PEBAX 6333. An inner lining 24 of high strength polymer material such as polyimide may be provided which extends to the start of the distal section 25 of the delivery member 11.

A supporting ribbon 26 extends through the distal section 25 with the proximal extremity thereof about 5 to about 15 mm being secured to the braided tubular structure 21 by suitable means such as solder or adhesive 27 within the wall of the proximal shaft section 30. The supporting ribbon 26 is generally about 6 to about 20 cm in total length and has a rectangular transverse cross-section of about 0.003-0.007 inch by 0.01-0.03 inch. The distal extremity of the supporting ribbon 26 is secured to the distal end of the delivery member 11 in a similar fashion. As shown in FIGS. 1 and 3, the braided tubular structure 21 extends into the distal section 25 of the delivery member 11 disposed about the supporting ribbon 26.

The distal section 25 of the delivery member 11 has an elongated opening 28 which allows a distal section 31 of the EP device 12 to be extended out and away from the distal section 25 of the delivery member 11 when an axial compressive force is applied to the proximal extremity of the EP device which extends out of the patient during the procedure. The length of the elongated opening 28 is generally the same length as the distal section 25, i.e. about 3 to about 20 cm. The width of the elongated opening 28 generally is greater than the diameter of the distal section 31 of the EP device 12 to allow for the ready outward movement of the EP device.

Figure 20:
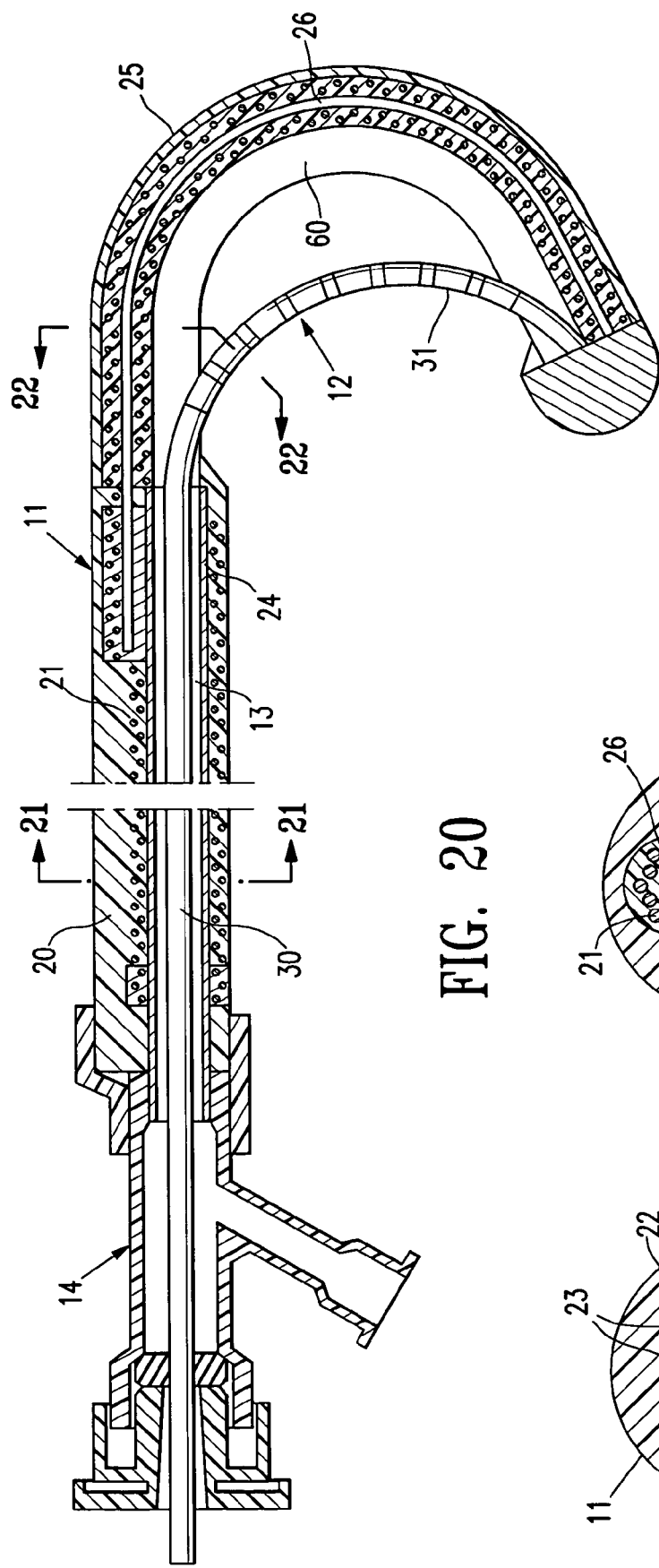
FIG. 20 is an elevational view, partially in section, of a mapping and ablation assembly embodying features of the invention.
Figure 21:
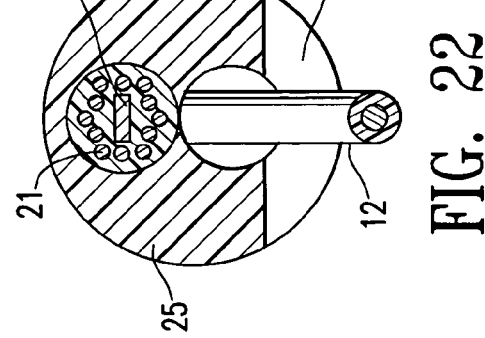
FIG. 21 is a transverse cross-sectional view of the assembly shown in FIG. 20 taken along the lines 21-21.
Figure 22:
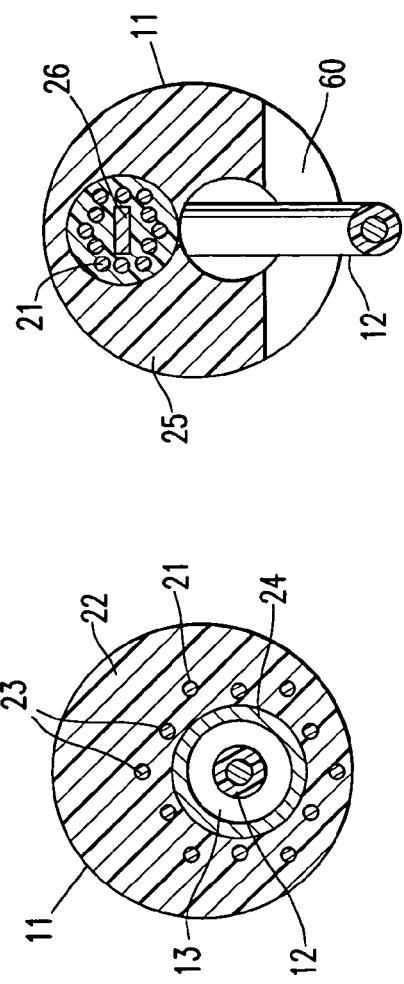
FIG. 22 is a transverse cross-sectional view of the assembly shown in FIG. 1 taken along the lines 22-22.

In an alternative embodiment illustrated in FIG. 20, the distal section 25 of the delivery member 11 is shapeable to a curved configuration with an elongated opening 60 along an inner side of the curved distal section 25. The distal end of the EP device 12 is secured within the distal end of the elongated delivery member. The distal section 31 of the EP device 12 is configured to extended out and away from the distal section 25 of the delivery member 11 through the elongated opening 60 when an axial elongating force is applied to the proximal extremity of the EP device which extends out of the patient during the procedure. Thus, when the EP device is displaced proximally relative to the delivery member, as when the proximal extremity of the EP device is pulled proximally, the distal section 31 of the EP device extends out the opening 60 in the distal section 25 along an inner side of the curved distal section 25. FIGS. 21 and 22 illustrate transverse cross sections of the assembly shown in FIG. 20 taken along lines 21-21 and 22-22, respectively.

In an alternative embodiment illustrated in FIG. 23, the elongated opening 28/60 is omitted and the delivery member 11 has an elongated depression along a side of the curved distal section 25, and an opening at a proximal end of the depression in fluid communication with the inner lumen 13. The depression is distal to the lumen 13 containing a proximal section of the EP device 12, and the EP device distal section 31 extends distally of the lumen 13 out the opening at the proximal end of the depression. The distal section 31 of the EP device is configured to extend away from the elongated depression when the EP device is displaced relative to the delivery member. FIG. 24 illustrates a transverse cross-sectional view of the assembly shown in FIG. 23 taken along line 24-24.

The EP device 12, as shown in FIGS. 1 and 4-5 includes a proximal shaft section 30 and a distal shaft section 31. The distal shaft section 31 has a plurality of mapping/ablation electrodes 32 with each of the electrodes electrically connected to separate electrical conductors 33 (shown in FIGS. 4-5). The electrodes 32 are generally not larger than about 1.5 mm (4 Fr.), preferably less than 1.3 mm (3.5 Fr.) in outer transverse dimensions. The electrode length may vary from about 1 to about 6 mm, preferably about 1 to about 3 mm, and the interelectrode spacing may vary from about 0.5 to about 4 mm, preferably about 0.5 to about 2 mm. The electrodes 32 may be in the form of metallic cylindrical bands, helical coils, arcuate bands or ribbons and the like. The only portion of the electrodes 32 which need exposure are those surfaces which are to be in contact with the inner surface of the heart chamber to detect electrical activity or effect a linear ablation.

A suitable EP device 12 shown in detail in FIGS. 4 and 5, has proximal and distal shaft sections 30 and 31, an electrical connector 34 on the proximal end of the device and eight electrodes 32 on the distal section 31 which are electrically connected to insulated electrical conductors as in copending application Ser. No. 09/104,752, entitled EP Catheter, filed Jun. 25, 1998, and Ser. No. 08/188,619, U.S. Pat. No. 5,509,411, entitled Intravascular Sensing Device, filed on Jan. 27, 1994, which are incorporated herein in their entireties by reference. Core member 35 extends to the distal end of the device which is secured to the distal end of coil 36 by suitable material such as a gold-tin solder (80% Au-20% Sn). The coil 36 is preferably a 90% Pt-10% Ir wire about 0.005 inch in diameter. Polyimide tubing 37, about 0.001 inch thick, jackets the core member 35 proximal to the coil 36 which is in turn covered with a fluoropolymer tube 38 such as THV 200G which is available from 3M. The braided electrical conductors 33 are formed of 36 AWG copper wire with each conductor having a polyimide insulating coating of about 0.0005 inch thick (0.013 mm). An equivalent number of polyester fibers 39 (e.g. Dacron® from Dupont) are braided with the electrical conductors 33. The braided structure formed by the electrical conductors 33 and the polyester strands 39 are covered by an additional fluoropolymer jacket or coating 40, preferably THV 200 g made by 3M. The electrodes 32 are helical coils which are preferably formed form 90% Pt-10% Ir wire about 0.005 inch (0.13 mm) in diameter.

The overall length of the delivery member 11, excluding the adapter 14, is about 110 to about 130 cm and the outer diameter is about 0.06 to about 0.08 inch (1.5-2.0 mm). The inner lumen 13 is slightly larger than the outer diameter of the EP device 12 and generally is about 0.035 to about 0.055 inch (0.9-1.4 mm). The EP device 12 has a working length of about 110-155 cm and a total length of about 135 to about 175 including the electrical connector 34.

The assembly of the invention may be introduced into the patient's vascular system, e.g. the femoral vein, percutaneously or by way of a cut-down, advanced therein and through the inferior vena cava until the distal section 25 is disposed within the right atrium. The supporting ribbon 26 in the distal shaft section 31 is shaped into a curved configuration so that it assumes the curved configuration when unrestrained within the heart chamber. With the supporting ribbon acting as a supporting surface, a compressive force is applied to the proximal extremity of the EP device which extends out of the patient to urge the device in the distal direction, causing the distal shaft section 31 of the EP device 12 to bow outwardly away from the distal section of the delivery member 11 and the support ribbon 26 therein. Alternatively, in the embodiment illustrated in FIG. 20 having an elongated opening 60 along an inner side of the curved distal section 25, the EP device is displaced proximally relative to the delivery member so that the distal section of the EP device extends through the elongated opening 60 in the distal section of the delivery member.

Figure 25A:
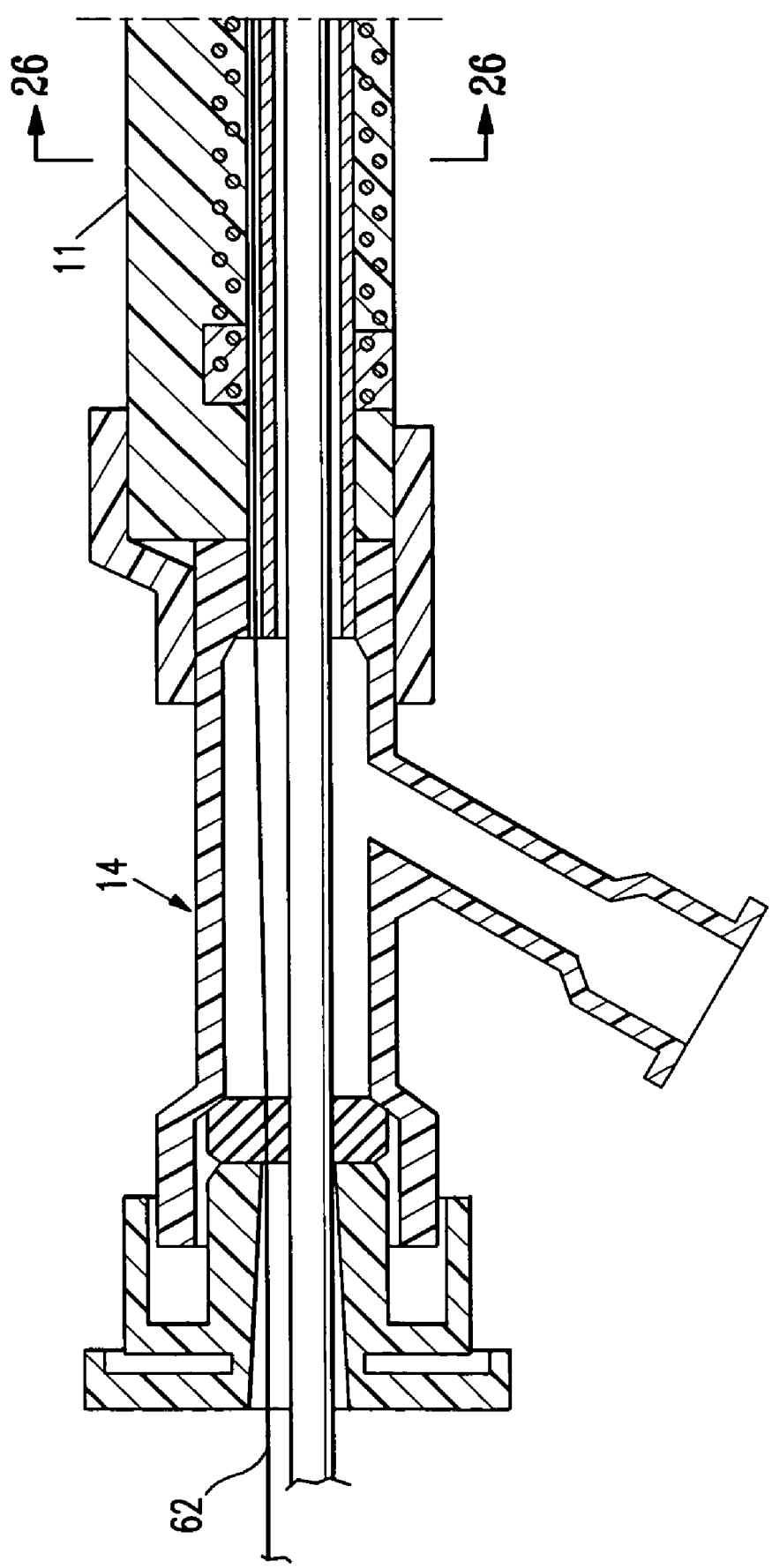
FIG. 25A is an elevational view, partially in section, of the proximal section of an alternative embodiment of the assembly shown in FIG. 20 having a deflection line.
Figure 25B:
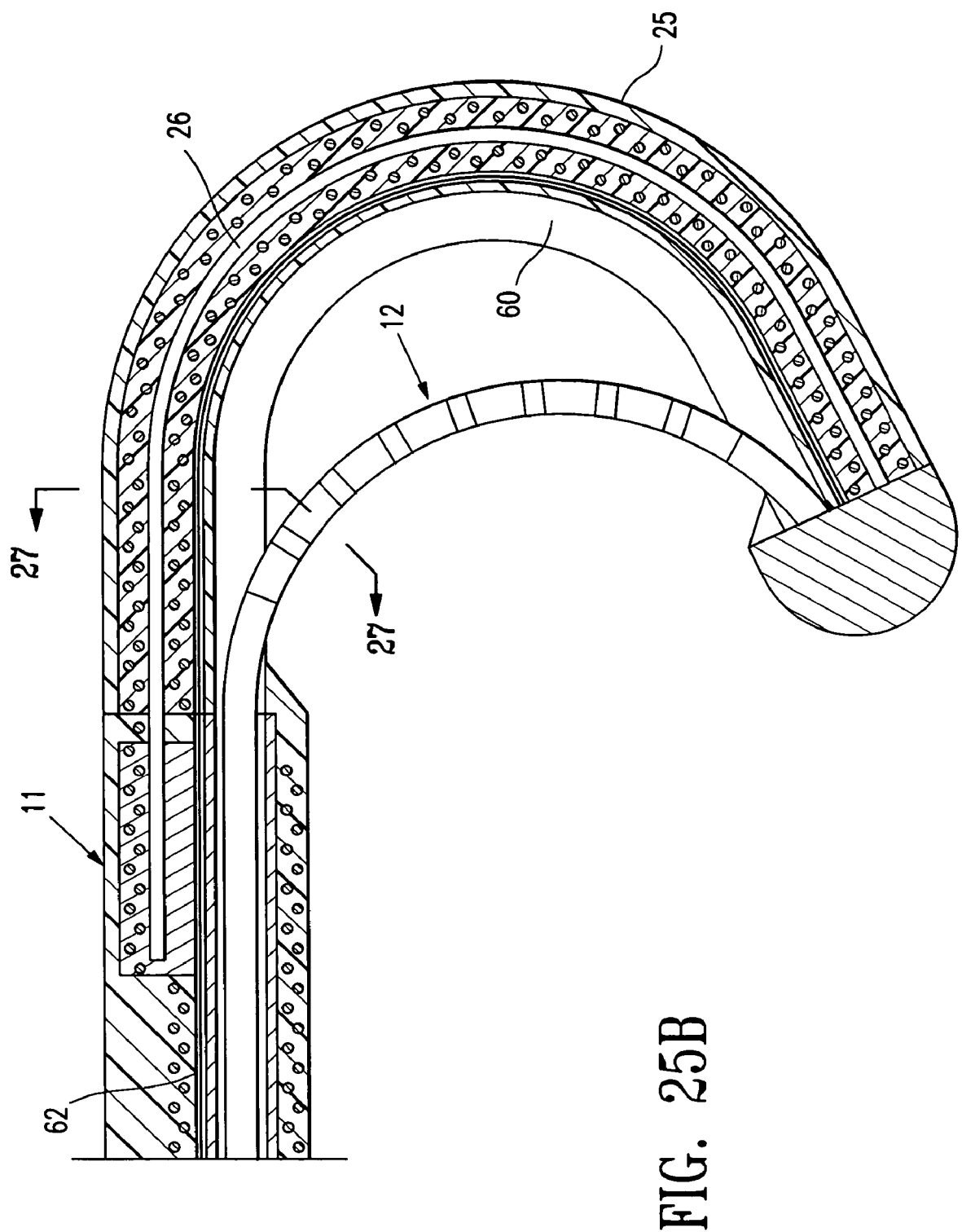
FIG. 25B is an elevational view, partially in section, of the distal section of an alternative embodiment of the assembly shown in FIG. 20 having a deflection line.
Figure 27:
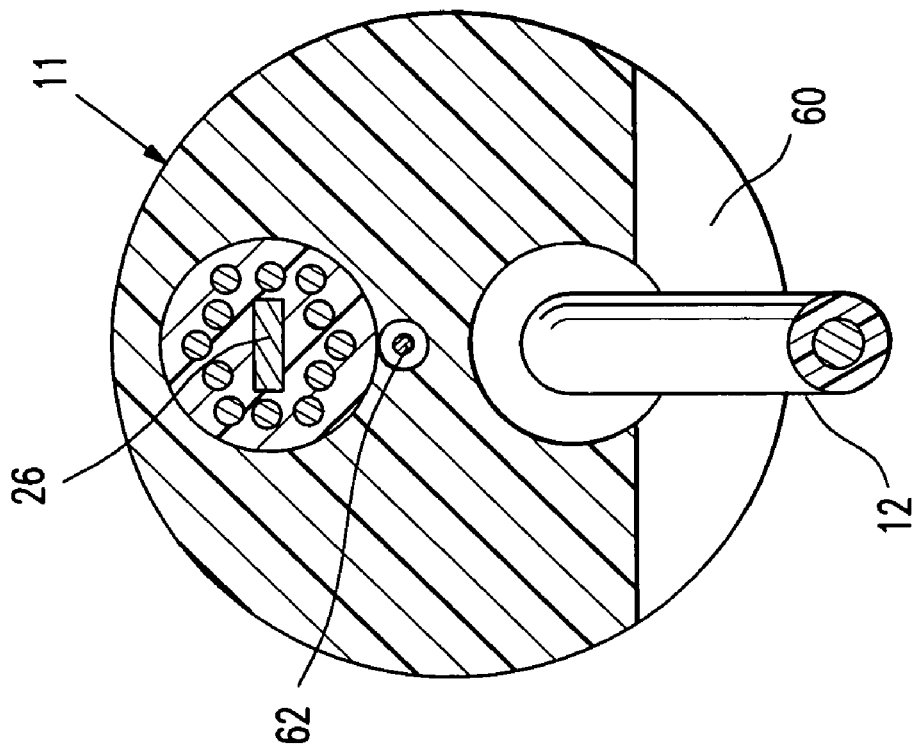
FIGS. 26 and 27 are transverse cross-sectional view of the assembly shown in FIG. 25 taken along lines 26-26 and 27-27, respectively.
Figure 26:
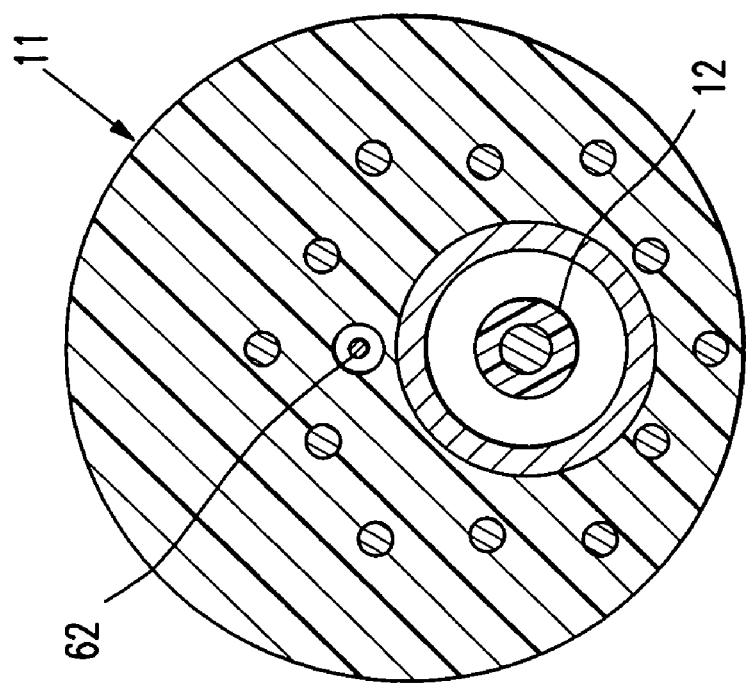
Figure 28:
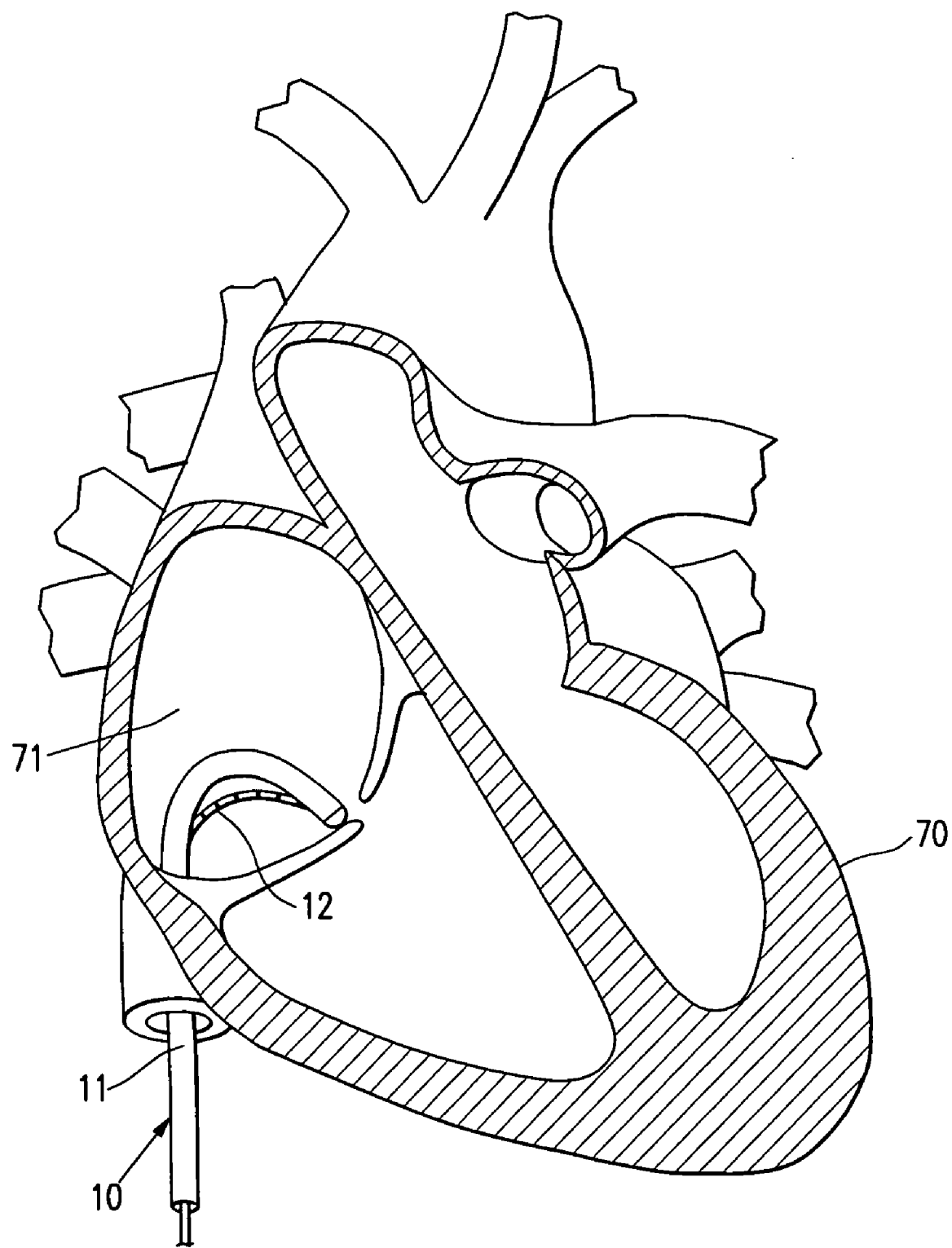
FIG. 28 is an elevational view partially in section of a human heart having the assembly shown in FIG. 20 within the right atrium.

The delivery member 11 distal section may be shaped or shapeable into a curved configuration. The terms shaped or shapeable should not be understood to require a permanently curved section, and instead also include a reversibly deflectable section. In one embodiment, the supporting ribbon 26 is shaped into a curved configuration, as illustrated in FIG. 20, so that it assumes the curved configuration when unrestrained within the heart chamber. In an alternative embodiment the delivery member 11 includes an elongated deflection line which deflects the delivery member distal section. In the embodiment illustrated in FIGS. 25-27, an elongated deflection line 62 is provided in a wall of the delivery member for deflecting the distal section 25 of the delivery member 11 relative to the delivery member longitudinal axis. The deflection line is displaced longitudinally relative to the delivery member to shape the delivery member distal section to the curved configuration. The deflection line may be used alone or in combination with the supporting ribbon to cause the distal section of the delivery member to assume the curved configuration. Moreover, the relative movement affected between the EP device and the delivery member may be used to produce additional deflection of the distal section 25 of the delivery member 11 relative to the delivery member longitudinal axis. FIG. 28 illustrates the assembly 10 shown in FIG. 20 within the right atrium 71 of a human heart 70. While the deflection line is shown in the embodiment of the delivery member 11 illustrated in FIGS. 25-27, it should be understood that the deflection line may be included in the alternative embodiments of the delivery member 11 illustrated in FIGS. 1, 20 and 23. With the delivery member distal section in the curved configuration illustrated in the figures, as for example in FIGS. 20 and 23, the EP device distal section is in a curved configuration that follows the curve of the delivery member distal section and extends away from the delivery member distal section to provide good contact against the heart wall.

Torquing the proximal section 30 of the delivery member 11, which extends out of the patient during the procedure, will cause the distal section 25 thereof to be rotatably displaced within the atrial chamber and allow the EP device 12 to be bowed outwardly in a wide variety of directions so electrical activity can be detected in a linear fashion and heart tissue can be linearly ablated at a number of locations within the chamber. When sensing electrical activity essentially all of the electrodes 32 can be simultaneously employed, but, when performing a linear ablation, the typical procedure is to direct the RF current to one or two electrodes at the most distal end of the EP device to perform the first ablation and then continue proximally one or two electrodes at a time until a linear ablation of desired length is obtained in the atrial chamber. This reduces the overall power requirements for the assembly.

The electrodes 32 heat up due to the conductive heat transfer from the tissue being ablated and it is preferred to bath the electrodes with cooling fluid during the procedure to minimize the formation of thrombus. While not shown in the drawings, thermocouples, thermistors or other temperature sensing means may be incorporated into the wall of the EP device 12 to detect the temperature of the electrodes or device wall. The flow of cooling fluid may be controlled to bathe the distal shaft section 31 of the EP device 12 based upon the temperature sensed by the temperature sensing means.

After the ablation, the electrodes 32 can be employed to detect electrical activity to ensure that the ablation has been effective in terminating the fibrillation or flutter. The electrodes 32 are much smaller in diametrical dimensions than prior ablation electrodes which are usually about 1.5 mm or larger. Surprisingly, it has been found that the much smaller electrodes of the present invention provide effective ablation through the atrial w-all without the power requirements of the prior electrodes. The elongated lesion formed by the linear ablation with the smaller electrodes, while much thinner than lesions formed with the prior larger electrodes, is quite effective in segregating heart tissue so as to terminate the fibrillation or flutter. Typically, the elongated lesion formed with the device of the present invention is about 3 to about 12 mm, usually about 5 to about 10 mm, in width.

FIGS. 6 and 7 illustrate an alternative embodiment to that shown in FIGS. 1-3 wherein a second lumen 41 is provided within the distal section of the delivery member in order to pass flushing or cooling fluids to the distal extremity of the delivery member. The spacing between the exterior of the EP device 12 and the inner surface of the inner lumen 13 of the delivery member 11 is minimized at location 42 so that a significant portion of fluid passing through the inner lumen 13 will pass through port 43 into the inner lumen 41. A discharge port 44 is provided in the distal end of the delivery member 11 for discharge of fluid from the inner lumen 41.

FIGS. 8-10 illustrate another embodiment similar in function to that shown in FIGS. 7-8 which has a second lumen 45 extending the length of the delivery member 11 which is in fluid communication with a second side arm 46 of the adapter 14. The other portions of the embodiment are similar to the embodiment shown in FIGS. 7-8 and are similarly numbered.

Figures 11, 12:
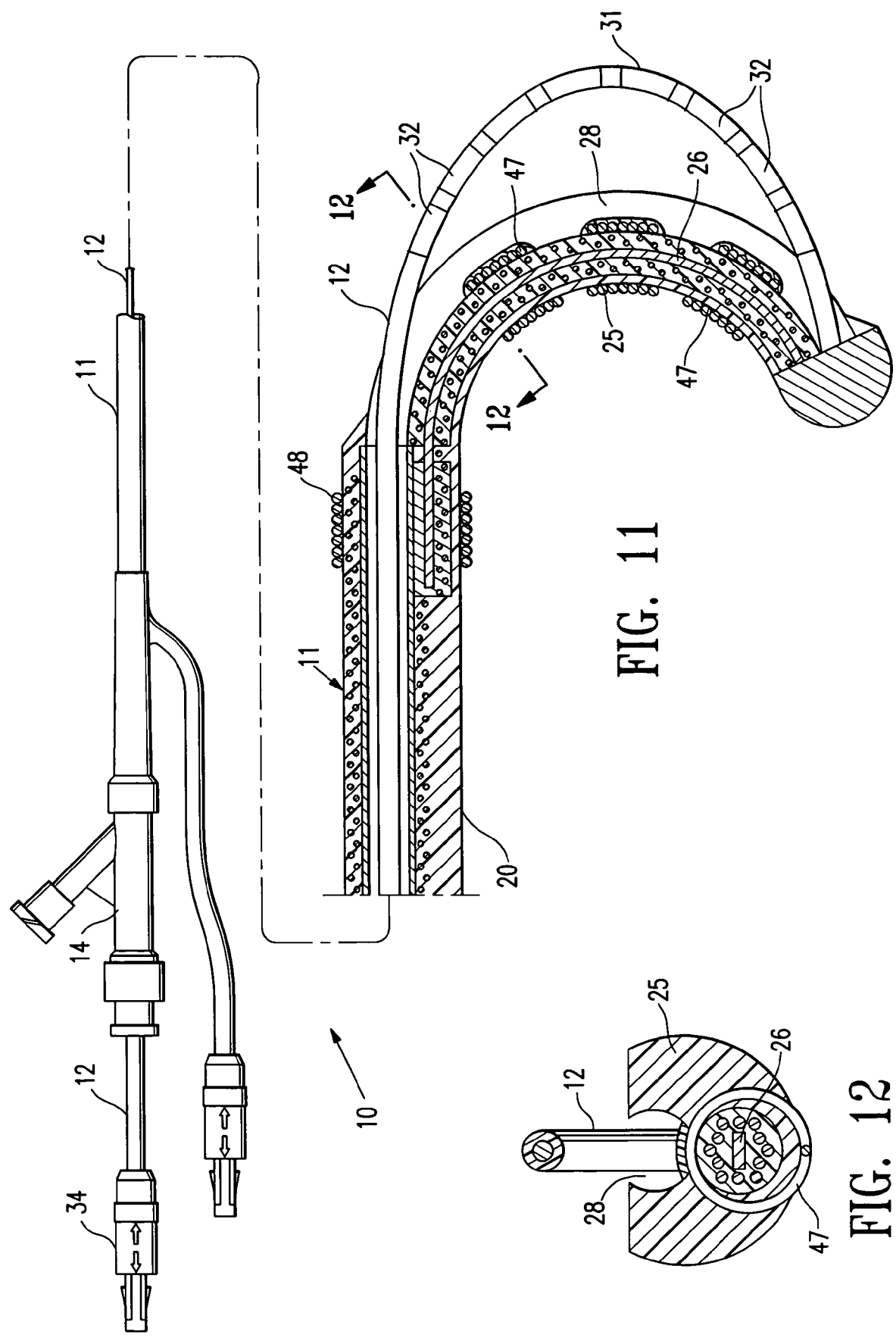
FIG. 11 is an elevational view, partially in section, of another alternative embodiment wherein the delivery member is provided with electrodes for sensing and/or ablation.
FIG. 12 is a transverse cross-sectional view of the embodiment shown in FIG. 11 taken along the lines 12-12.

FIGS. 11-12 depict yet another embodiment similar in most regards to that shown in FIG. 1 except that the delivery member 11 is provided with a plurality of electrodes 47 on the distal section 25 and at least one electrode 48 on the proximal shaft section 20. In this embodiment, the surface of the electrodes 47 on the inside of the curved distal section 25 need to be exposed. The electrodes 47 and 48 may be helical coils as shown or cylindrical tubes or arcuate ribbon or bands provided on the inside curve of the distal section 25. Individual electrical conductors (not shown) may be incorporated into the braided tubular structure 21 and electrically connected by their distal ends to the electrodes 47 and 48 and by their proximal ends to one or more electrical connectors configured to be electrically connected to a high frequency electrical energy source.

Another alternative embodiment of the invention is shown in FIGS. 13, 14A and 14B wherein the EP device 12 is provided with an inner lumen 49 for fluid delivery. An adapter 50 is secured to the proximal end of the EP device 12 to facilitate introduction of fluid to the inner lumen 49. In FIG. 14A the lumen 49 is off-set from the electrical conductors 51 which are braided about the core 52, whereas, in FIG. 14B the lumen 49 is formed by the braided conductors 51 within a polymer matrix 53. The embodiment of FIG. 14B does not have a core member 52 as in FIG. 14A. A discharge port 54 is provided in the distal end of the EP device 12 which is in fluid communication with the inner lumen 49.

Figures 15, 16:
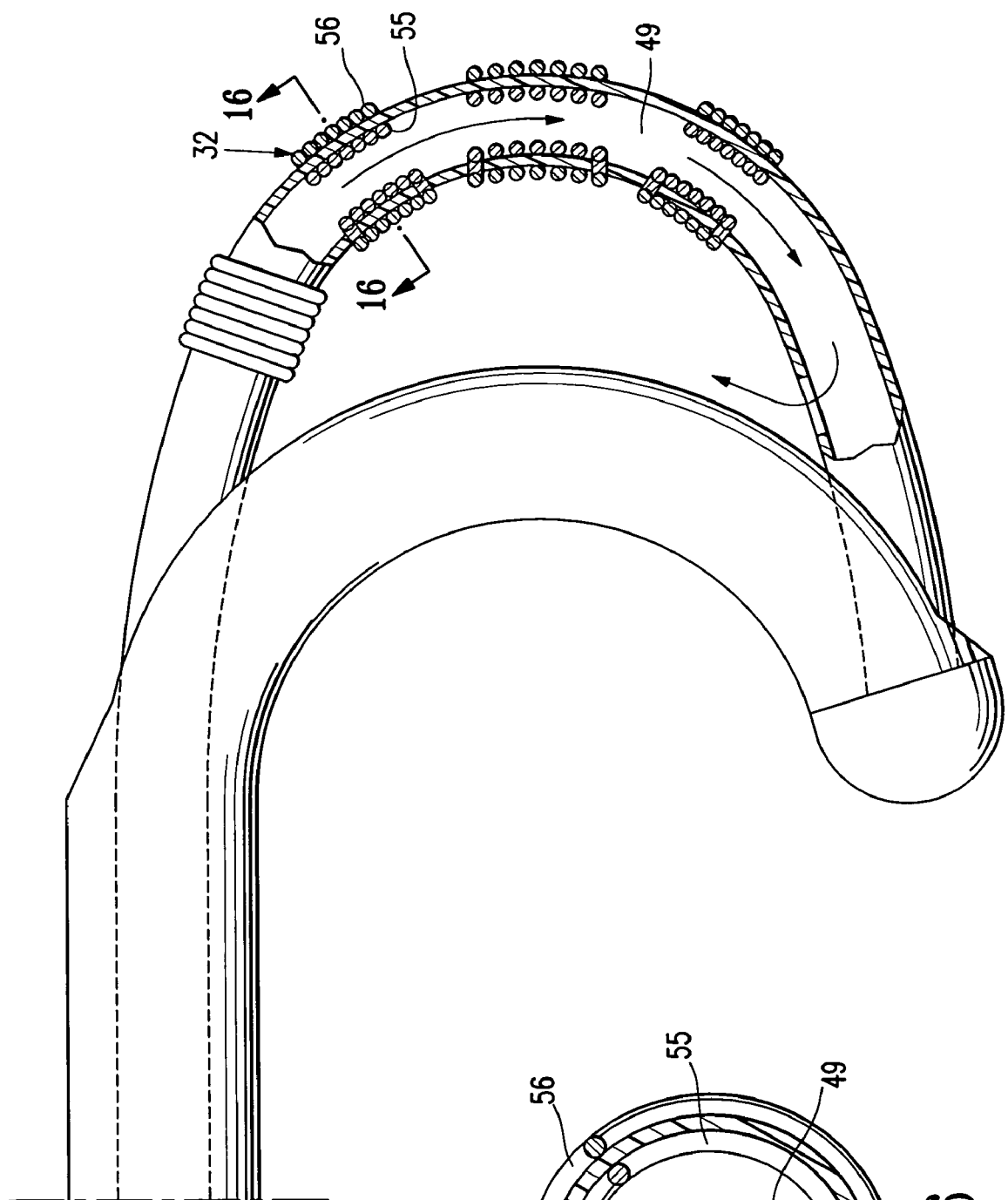
FIG. 15 is an elevational view, partially in section, of a distal section of an alternative embodiment wherein the EP device is provided with an inner lumen for passage of fluid coolant.
FIG. 16 is a transverse cross-sectional view taken along the lines 16-16.

Alternative electrode details are illustrated in FIGS. 15 and 16 where the electrodes 32 are formed by a pair of inner and outer coils 55 and 56 which are secured together at each end by solder, adhesive or the like. The electrodes 32 are cooled by fluid flowing through the inner lumen 49. The coils may be expanded in the longitudinal direction to allow passage of fluid there through. A passageway (not shown) must be provided through the wall of the EP device to facilitate the passage of fluid. A single coil may be used for each electrode rather than a pair of coils 55 and 56 as shown.

Figure 17:
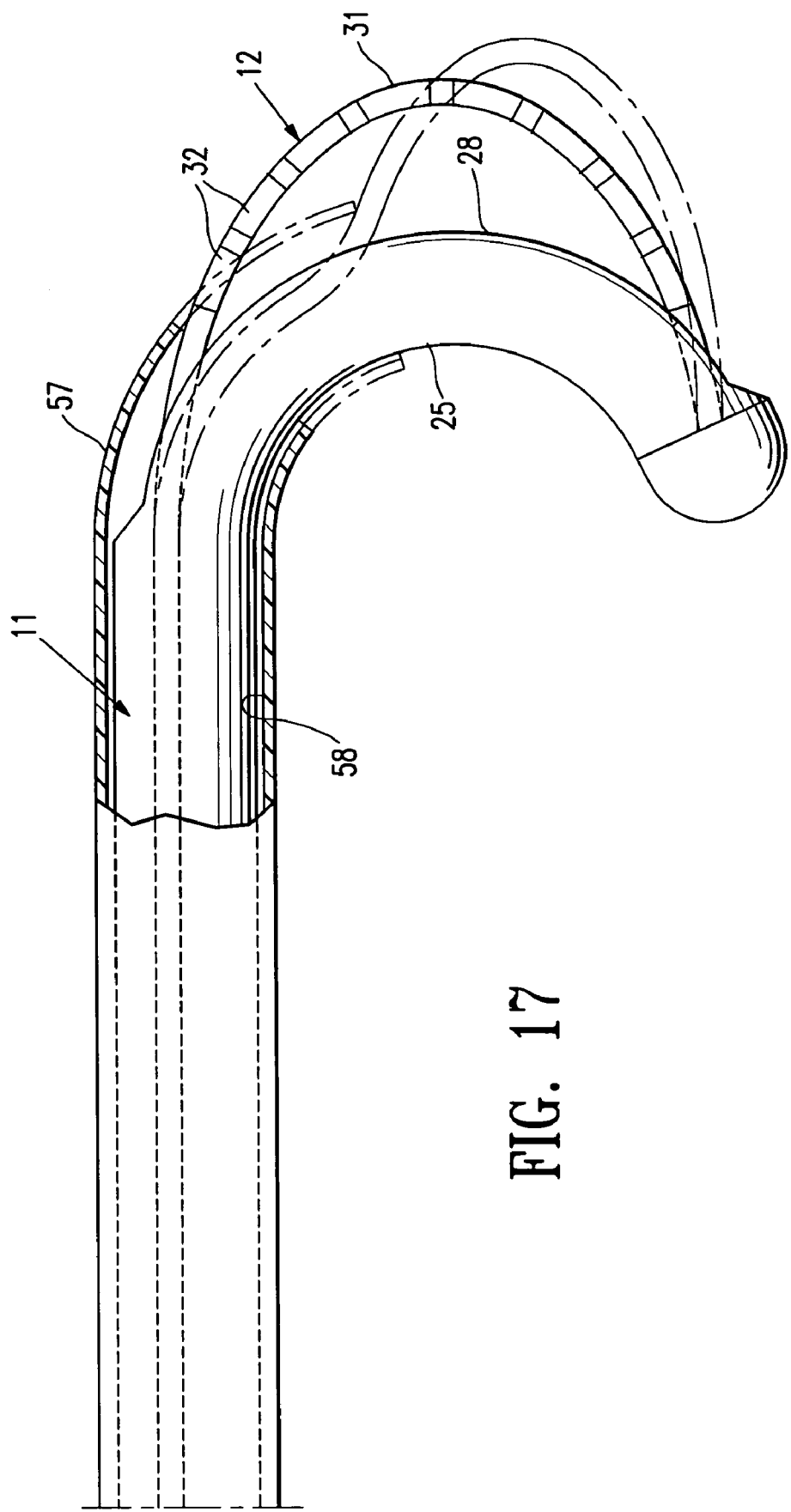
FIG. 17 is an elevational view, partially in section, of a distal section of an alternative embodiment wherein an outer sheath is disposed about the assembly which is longitudinally movable to control the effective length of the elongated opening in the distal section of the delivery member.
Figure 29:
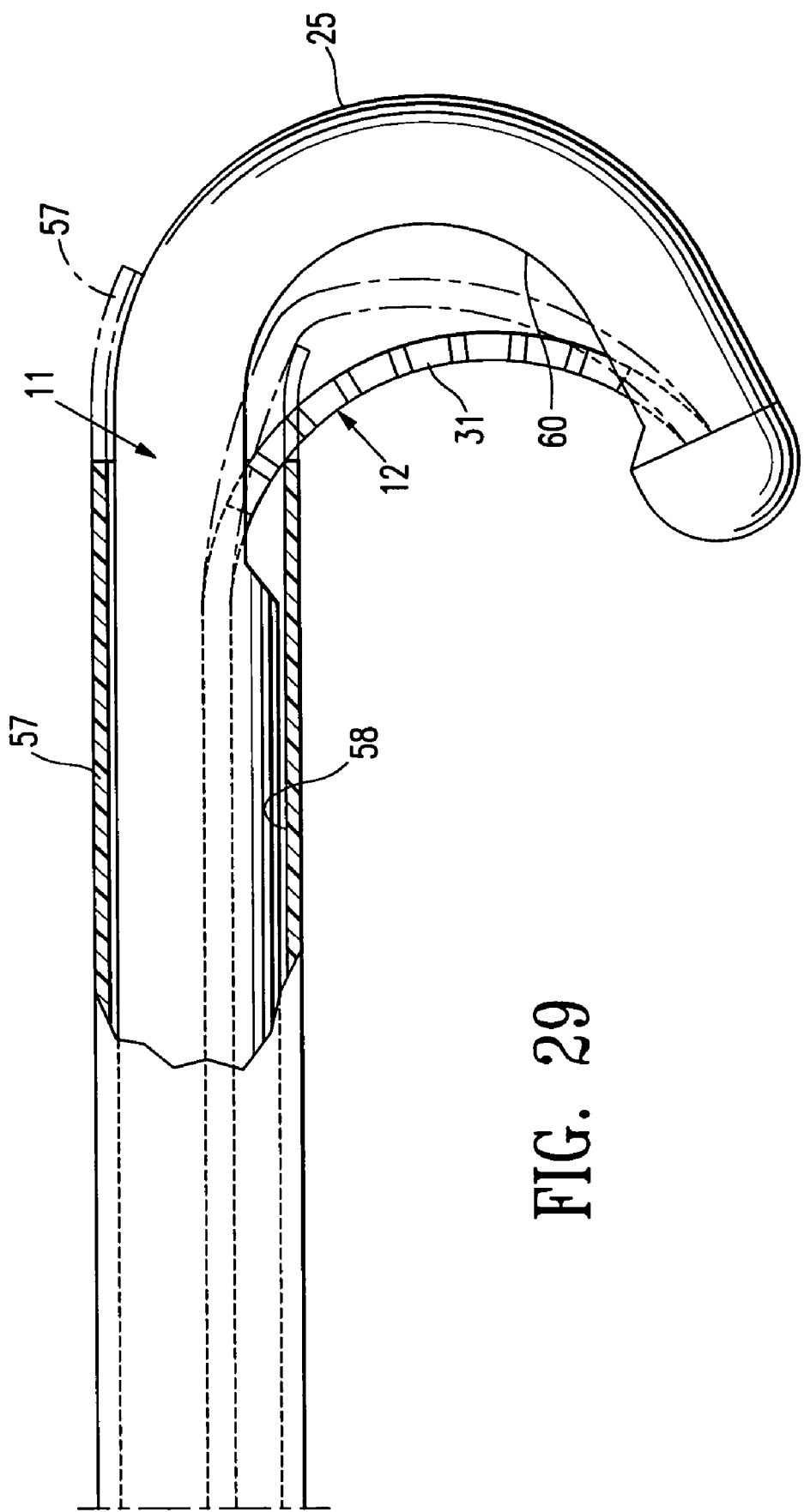
FIG. 29 is an elevational view, partially in section, of a distal section of an alternative embodiment of the assembly shown in FIG. 20 wherein an outer sheath is disposed about the assembly which is longitudinally movable to control the effective length of the elongated opening in the distal section of the delivery member.

In some instances it is desirable to change the curvature of the distal shaft section 31 of the EP device 12 when the distal end of the device is within the heart chamber to provide a better fit between the distal shaft section 31 and the inner surface of a heart chamber. To facilitate such changes, an outer sheath 57 may be provided about the exterior of the delivery member to effectively shorten the elongated opening 28/60 in the distal section 25 of the delivery member 11 as shown in FIGS. 17 and 29. By shortening the elongated opening 28 the radius of curvature is reduced, as shown in phantom in FIGS. 17 and 29. Fluid may be passed through the inner lumen 58 of the sheath 57 to cool the electrodes 32 during delivery of RF electrical energy. A variety of other means may be employed to effectively shorten the elongated opening 28.

FIGS. 19 and 18 illustrate another method of cooling the electrodes 32 on the distal section of the EP device 12 where a flushing sheath 59 is slidably disposed about the EP device. In this embodiment, the sheath 59 can be longitudinally moved along the shaft of the EP device to expose one or more electrodes 32. Fluid passing over the exposed electrode(s) while electrical energy is being delivered will cool the electrodes sufficiently to avoid thrombus formation. Usually, electrical energy is not directed to the entire array of electrodes at the same time due to the rather large power requirements for such delivery. Electrical energy is preferably delivered to one or two of the most distal electrodes while fluid is delivered thereto until the lesion of desired length is formed. The sheath 59 is then pulled proximally to expose additional electrodes 32, electrical energy is delivered to one or two additionally exposed electrodes while cooling fluid flows out of the distal end of the sheath 59. This procedure continues sequentially delivering electrical energy to the more proximal electrodes until a linear ablation of the desired length is formed in the wall of the patient's heart. The individual electrodes 32 may be used to detect electrical activity after each individual ablation and after the entire linear ablation procedure has been completed to determine if the fibrillation or flutter has been terminated.

While the invention has been described herein in terms or certain preferred embodiments directed to the treatment of atrial fibrillation and flutter, those skilled in the art will recognize that the invention may be employed in a wide variety of procedures where an elongated lesion is to be formed. Moreover, although individual features of embodiments of the invention may be shown in some of the drawings and not in others, those skilled in the art will recognize that individual features of one embodiment of the invention can be combined with any or all the features of another embodiment. A variety of modifications and improvements may be made to the present invention without departing from the scope thereof.

What is claimed is:

1. An intravascular assembly for forming a continuous lesion within a chamber of a patient's heart, comprising:
   a) an elongated delivery member having proximal and distal ends, an inner lumen extending therein to the distal end, a distal section shapeable into a curved configuration having an inner side and an outer side, an elongated opening in the inner side of the curved distal section in communication with the inner lumen and an elongated support element which is fixed along a length of the distal section coextensive with at least part of the elongated opening; and
   b) an elongated electrophysiological device disposed within the inner lumen of the elongated delivery member, having a distal end secured within the distal end of the elongated delivery member, and having a plurality of emitting electrodes on a distal portion thereof, and which is configured to extend out of the elongated opening along the inner side of the delivery member curved distal section upon relative movement between the delivery member and the elongated EP device, a plurality of electrical conductors having proximal and distal ends with individual electrical conductors being electrically connected by their distal ends to emitting electrodes on the distal portion of the electrophysiological device and by their proximal ends to an electrical connector suitable for connection to a source of high frequency electrical energy.

2. The intravascular assembly of claim 1 wherein the distal section of the elongated delivery member is shaped to facilitate entry and positioning within the patient's heart chamber.

3. The intravascular assembly of claim 1 wherein the support element within the distal section is a metallic ribbon.

4. The intravascular assembly of claim 3 wherein the metallic ribbon has a flat surface facing the elongated opening.

5. The intravascular assembly of claim 3 wherein a multi-arm adapter is provided on the proximal end of the assembly which has an arm with an inner lumen in fluid communication with the lumen for delivery of the cooling fluid.

6. The intravascular assembly of claim 1 wherein the electrodes on the distal portion of the electrophysiological device are not more than 1.35 mm in diameter.

7. The intravascular assembly of claim 1 including a longitudinally movable sheath disposed about the delivery member to control the length of the elongated opening, which is exposed.

8. The intravascular assembly of claim 7 wherein the sheath has a curved distal extremity.

9. The intravascular assembly of claim 1 including a longitudinally movable sheath disposed about the EP device having a proximal end configured to be connected to a source of fluid and a distal end extending over the distal extremity of the EP device.

10. The intravascular assembly of claim 1 including a second inner lumen extending within at least the distal section of the elongated delivery member to a discharge port in the distal end of the elongated delivery member.

11. The intravascular assembly of claim 10 wherein the second inner lumen extends from the proximal end of the elongated delivery member to the distal end thereof.

12. The intravascular assembly of claim 1 wherein the elongated delivery member is provided with at least one electrode on the distal section thereof.

13. The intravascular assembly of claim 1 wherein the distal section of the elongated delivery member is provided with a lumen for delivery of cooling fluid to the distal end of the assembly.

14. The intravascular assembly of claim 13 wherein the lumen for delivery of the cooling fluid extends to the proximal end of the assembly.

15. The intravascular assembly of claim 1 including an elongated deflection line secured to the distal end of the delivery member.

16. A method for treating a patient's heart for fibrillation or flutter comprising:
   a) providing a intravascular assembly including
      an elongated delivery member having proximal and distal ends, an inner lumen extending therein to the distal end, a distal section shapeable to a curved configuration having an inner side and an outer side, an elongated opening in the inner side of the curved distal section in communication with the inner lumen, and an elongated support element which is fixed along a length of the distal section coextensive with at least part of the elongated opening; and
      an elongated electrophysiological device disposed within the inner lumen of the elongated delivery member, having a plurality of emitting electrodes on a distal portion thereof, and which is configured to extend out of the elongated opening along the inner side of the delivery member curved distal section upon relative movement between the delivery member and the elongated electrophysiological device;
   b) introducing the intravascular assembly into the patient's vasculature and advancing the assembly therein until the distal portion of the assembly is disposed within a chamber of the patient's heart;
   c) effecting relative movement between the electrophysiological device and the delivery member by displacing the electrophysiological device proximally relative to the delivery member so that the distal section of the electrophysiological device extends through the elongated opening in the distal section of the delivery member;
   d) contacting the extended distal section of the electrophysiological device with a desired surface of the heart chamber;
   e) delivering high frequency electrical energy to at least one electrode on the electrophysiological device to form a first lesion on the surface of the heart chamber; and
   f) delivering high frequency electrical energy to at least one other electrode on the electrophysiological device to form at least a second lesion on the surface of the heart chamber adjacent to a previously formed lesion thereon.

17. The method of claim 16 wherein the electrodes on the electrophysiological device are bathed in cooling fluid when emitting high frequency electrical energy.

18. The method of claim 16 wherein an outer sheath is disposed about the intravascular assembly and the longitudinal position of the outer sheath about the intravascular assembly is adjusted to control the length of the elongated opening in the elongated delivery member which in turn controls the curvature of the distal section of the electrophysiological device which extends out of the elongated opening.

19. An intravascular assembly for forming a continuous lesion within a chamber of a patient's heart, comprising:
   a) an elongated delivery member having proximal and distal ends, an inner lumen extending within at least a section of the delivery member, a distal section shapeable into a curved configuration having an inner side and an outer side; and
   b) an elongated electrophysiological device having a distal end secured to the distal end of the elongated delivery member, and having a distal section shapeable into a curved configuration which is configured to follow the delivery member curved distal section and extend away from the delivery member curved distal section, and having a plurality of emitting electrodes on a distal portion thereof, a plurality of electrical conductors having proximal and distal ends with individual electrical conductors being electrically connected by their distal ends to emitting electrodes on the distal portion of the electrophysiological device and by their proximal ends to an electrical connector suitable for connection to a source of high frequency electrical energy.

20. The intravascular assembly of claim 19 wherein the delivery member distal section is deflectable and including an elongated deflection line secured to the distal end of the delivery member.

21. A method for treating a patient's heart for fibrillation or flutter comprising:
   a) providing an intravascular assembly including
      an elongated delivery member having proximal and distal ends, an inner lumen extending within at least a section of the delivery member, a distal section shapeable into a curved configuration having an inner side and an outer side; and
      an elongated electrophysiological device having a distal end secured to the distal end of the elongated delivery member, and having a distal section shapeable into a curved configuration which is configured to follow the delivery member curved distal section and extend away from the delivery member curved distal section, and having a plurality of emitting electrodes on a distal portion thereof, a plurality of electrical conductors having proximal and distal ends with individual electrical conductors being electrically connected by their distal ends to emitting electrodes on the distal portion of the electrophysiological device and by their proximal ends to an electrical connector suitable for connection to a source of high frequency electrical energy;
   b) introducing the intravascular assembly into the patient's vasculature and advancing the assembly therein until the distal portion of the assembly is disposed within a chamber of the patient's heart;
   c) deflecting the distal sections of the delivery member and the electrophysiological device into the curved configuration so that the distal section of the electrophysiological device follows the distal section of the delivery member;
   d) effecting relative movement between the electrophysiological device and the delivery member by displacing the electrophysiological device proximally relative to the delivery member so that the distal section of the electrophysiological device extends away from the distal section of the delivery member;
   e) contacting the extended distal section of the electrophysiological device with a desired surface of the heart chamber;
   f) delivering high frequency electrical energy to at least one electrode on the electrophysiological device to form a first lesion on the surface of the heart chamber; and
   g) delivering high frequency electrical energy to at least one other electrode on the electrophysiological device to form at least a second lesion on the surface of the heart chamber adjacent to a previously formed lesion thereon.

22. An intracorporeal assembly for forming a continuous lesion, comprising:
   a) an elongated delivery member having proximal and distal ends, a distal section shapeable into a curved configuration having an inner side and an outer side, an elongated opening in one of the inner or outer sides of the curved distal section and an elongated support element which is fixed along a length of the distal section coextensive with at least part of the elongated opening; and
   b) an elongated electrophysiological device which is disposed within the elongated delivery member, which has a distal end secured within the distal end of the elongated delivery member, and which has a plurality of emitting electrodes on a distal portion thereof, and which is configured to extend out of the elongated opening along the inner or outer side of the delivery member curved distal section upon relative movement between the delivery member and the elongated electrophysiological device.

23. The intracorporeal assembly of claim 22 wherein the elongated delivery member has an inner lumen extending therein.

24. The intracorporeal assembly of claim 23 wherein the side opening is in communication with the inner lumen.

25. The intracorporeal assembly of claim 23 wherein elongated electrophysiological device is disposed within the inner lumen of the elongated delivery member.

26. The intracorporeal assembly of claim 22 wherein elongated opening is in the inner side of the elongated delivery member.

27. The intracorporeal assembly of claim 22 wherein the electrophysiology device has a plurality of electrical conductors having proximal and distal ends with individual electrical conductors being electrically connected by their distal ends to emitting electrodes on the distal portion of the electrophysiological device and by their proximal ends to an electrical connector suitable for connection to a source of high frequency electrical energy.

28. The intracorporeal assembly of claim 22 wherein the distal section of the elongated delivery member is shaped to facilitate entry and positioning within the patient's heart chamber.

29. The intracorporeal assembly of claim 22 wherein the support element within the distal section is a metallic ribbon.

30. The intracorporeal assembly of claim 29 wherein the metallic ribbon has a flat surface facing the elongated opening.

31. The intracorporeal assembly of claim 22 wherein the electrodes on the distal portion of the electrophysiological device are not more than 1.35 mm in diameter.

32. The intracorporeal assembly of claim 22 including a longitudinally movable sheath disposed about the delivery member to control the length of the elongated opening.

33. The intracorporeal assembly of claim 32 wherein the sheath has a curved distal extremity.

34. The intracorporeal assembly of claim 22 including a longitudinally movable sheath disposed about the EP device having a proximal end configured to be connected to a source of fluid and a distal end extending over the distal extremity of the EP device.

35. The intracorporeal assembly of claim 22 including a second inner lumen extending within at least the distal section of the elongated delivery member to a discharge port in the distal end of the elongated delivery member.

36. The intracorporeal assembly of claim 35 wherein the second inner lumen extends from the proximal end of the elongated delivery member to the distal end thereof.

37. The intracorporeal assembly of claim 22 including a longitudinally movable outer sheath disposed about the intravascular device to control the length of the elongated opening which is exposed.

38. The intracorporeal assembly of claim 22 wherein the elongated delivery member is provided with at least one electrode on the distal section thereof.

39. The intracorporeal assembly of claim 22 wherein the distal section of the elongated delivery member is provided with a lumen for delivery of cooling fluid to the distal end of the assembly.

40. The intracorporeal assembly of claim 39 wherein the lumen for delivery of the cooling fluid extends to the proximal end of the assembly.

41. The intracorporeal assembly of claim 39 wherein a multi-arm adapter is provided on the proximal end of the assembly which has an arm with an inner lumen in fluid communication with the lumen for delivery of the cooling fluid.

42. The intracorporeal assembly of claim 22 including an elongated deflection line secured to the distal end of the delivery member.

43. A method for treating a patient's heart, comprising:
    a) providing an intracorporeal assembly including
        an elongated delivery member which has proximal and distal ends, a distal section shapeable into a curved configuration having an inner side and an outer side; and
        an elongated electrophysiological device having a distal end secured to the distal end of the elongated delivery member, and having a distal section shapeable into a curved configuration which is configured to follow the delivery member curved distal section and extend away from the delivery member curved distal section, and having a plurality of emitting electrodes on a distal portion thereof;
    b) introducing the intravascular assembly into the patient's vasculature and advancing the assembly therein until the distal portion of the assembly is disposed tissue of the patient's heart;
    c) deflecting the distal sections of the delivery member and the electrophysiological device into the curved configuration so that the distal section of the electrophysiological device follows the distal section of the delivery member;
    d) effecting relative movement between the electrophysiological device and the delivery member by displacing the electrophysiological device proximally relative to the delivery member so that the distal section of the electrophysiological device extends through the elongated opening in the side of the delivery member away from the distal section thereof;
    e) contacting the extended distal section of the electrophysiological device with desired heart tissue; and
    f) delivering high frequency electrical energy to a plurality of electrodes on the electrophysiological device to form a first lesion on the surface of the heart tissue.

44. The method of claim 43 wherein high frequency electrical energy is delivered to at least one of the electrodes on the electrophysiological device to form at least a second lesion on the surface of the heart tissue adjacent to a previously formed lesion thereon.

45. A method for treating a patient's heart, comprising the steps of:
    a) providing an intracorporeal assembly including
        an elongated delivery member which has proximal and distal ends, a distal section shapeable into a curved configuration having an inner side and an outer side; and
        an elongated electrophysiological device having a distal end secured to the distal end of the elongated delivery member, and having a distal section shapeable into a curved configuration which is configured to follow the delivery member curved distal section and extend away from the delivery member curved distal section, and having a plurality of emitting electrodes on a distal portion thereof;
    b) introducing the intravascular assembly into the patient's vasculature and advancing the assembly therein until the distal portion of the assembly is disposed tissue of the patient's heart;
    c) deflecting the distal sections of the delivery member and the electrophysiological device into the curved configuration so that the distal section of the electrophysiological device follows the distal section of the delivery member;
    d) effecting relative movement between the electrophysiological device and the delivery member by displacing the electrophysiological device proximally relative to the delivery member so that the distal section of the electrophysiological device extends through the elongated opening in the side of the delivery member away from the distal section thereof;
    e) contacting the extended distal section of the electrophysiological device with desired heart tissue; and
    f) delivering high frequency electrical energy to a plurality of electrodes on the electrophysiological device to form a first lesion on the surface of the heart tissue.

46. The method of claim 45 including the step of delivering high frequency electrical energy delivered to at least one of the electrodes on the electrophysiological device to form at least a second lesion on the surface of the heart tissue adjacent to a previously formed lesion thereon.

* * * * *